United States Patent [19]
Tuy

[11] Patent Number: 6,104,775
[45] Date of Patent: Aug. 15, 2000

[54] 3D IMAGE RECONSTRUCTION FOR HELICAL PARTIAL CONE BEAM SCANNERS USING WEDGE BEAM TRANSFORM

[75] Inventor: Heang K. Tuy, Chesterland, Ohio

[73] Assignee: Picker International, Inc., Highland Heights, Ohio

[21] Appl. No.: 09/181,980

[22] Filed: Oct. 29, 1998

[51] Int. Cl.[7] .................................................. A61B 6/03
[52] U.S. Cl. ................................ 378/4; 378/15; 378/901
[58] Field of Search ................................ 378/4, 15, 901

[56] References Cited

U.S. PATENT DOCUMENTS

| | | | |
|---|---|---|---|
| 4,789,929 | 12/1988 | Nishimura et al. | 378/15 |
| 5,073,911 | 12/1991 | Ozaki et al. | 378/17 |
| 5,090,037 | 2/1992 | Toth et al. | 378/4 |
| 5,377,250 | 12/1994 | Hu | 378/15 |
| 5,404,293 | 4/1995 | Weng et al. | 378/15 |
| 5,485,493 | 1/1996 | Heuscher et al. | 378/15 |
| 5,625,660 | 4/1997 | Tuy | 378/15 |
| 5,740,224 | 4/1998 | Müller et al. | 378/11 |

OTHER PUBLICATIONS

"Technique and Arrangement for Tomographic Imaging," PCT Application of Danielsson, et al. (Jan. 13, 1998).

Defrise, et al., "A Cone–Beam Reconstruction Algorithm Using Shift–Variant Filtering and Cone–Beam Backprojection," *IEEE Transactions on Medical Imaging*, (Mar. 1994) vol. 13, No. 1, pp. 186–195.

*Primary Examiner*—David V. Bruce
*Attorney, Agent, or Firm*—Fay, Sharpe, Fagan, Minnich & McKee, LLP

[57] ABSTRACT

A method of image reconstruction from wedge beam data includes collecting cone beam data in two-dimensional arrays. The collected data corresponds to rays of penetrating radiation diverging in two dimensions from a common vertex which travels along a curve. Each element of the data is related to line integrals of an object being reconstructed taken along each ray. A local coordinate system is defined having three mutually orthogonal axes and an origin at the vertex. The third axis of the local coordinate system extends in a direction tangential to the curve at the vertex. The collected data is rebinned into a wedge beam format wherein sets of parallel rays are grouped to define planes of radiation that angularly diverge from a common axis. A one-dimensional convolution of the rebinned data is computed in the local coordinate system along a direction parallel to the third axis. Finally, the convolved data is weighted and three-dimensionally backprojected. In a preferred embodiment, the curve defines a helical path, and the kernel for the one-dimensional convolution of the rebinned data is a ramp convolver.

17 Claims, 4 Drawing Sheets

3D IMAGE RECONSTRUCTION FOR HELICAL PARTIAL CONE BEAM SCANNERS USING WEDGE BEAM TRANSFORM

BACKGROUND OF THE INVENTION

The present invention relates to the art of image reconstruction. It finds particular application in conjunction with CT scanners, and will be described with particular reference thereto. However, it is to be appreciated that the present invention is also amenable to other like applications.

Conventionally, spiral CT scanners include an x-ray source which projects a thin slice or beam of radiation. The x-ray source is mounted for rotational movement about a subject who is moving along the axis of rotation. An arc or ring of radiation detectors receive radiation which has traversed the subject. Data from the radiation detectors represents a single spiraling slice through the subject. The data from the detectors is reconstructed into a three-dimensional image representation.

For faster data collection, a pair or more of radiation detectors can be disposed next to each other. This enables two or more slices of data to be collected concurrently. However, like the single slice scanner, only intra-slice data is used in the reconstruction process.

One of the difficulties with such prior art scanners is that they place major stress on the x-ray generator. When a solid geometric shape of x-rays, such as a cone, are generated, the x-rays pass through a volumetric region of the subject. In true cone beam reconstruction, truncation of the data is not permitted. These x-rays pass along known rays, both within traditional planes and at acute angles through several planes. The radiation passing along rays at an angle to the central plane were previously lost to collimation. By utilizing the radiation previously lost in collimation to generate useful diagnostic information, the load on the x-ray generator is reduced.

However, images reconstructed from data collected along divergent beams tend to have artifacts. One way of minimizing the divergent ray artifacts is to minimize the number of rings, i.e., limit the width of the cone beam. Of course, limiting the width of the cone beam partially defeats the original intent.

Although the additional radiation supplied by the cone beam is beneficial in imaging, it has the detrimental side effect of increasing the dosage to the subject. On the other hand, the high dosage enables a volume to be reconstructed with fewer rotations of the cone beam.

In U.S. Pat. No. 5,625,660 (hereinafter the '660 patent), commonly assigned and incorporated herein by reference, an image reconstruction technique for helical partial cone-beam data is disclosed. However, that technique divides the data stream into two parts which are processed separately and then recombined. In general, this is less efficient and more complicated than processing a single data stream.

In H. Tuy's U.S. patent application Ser. No. 09/164,013 entitled "3D Image Reconstruction for Helical Partial Cone Beam Data" and filed Sep. 30, 1998 which is commonly assigned and incorporated by reference here, a single data stream image reconstruction technique for helical partial cone-beam data is disclosed. While relatively more efficient and less complicated than the '660 patent, this technique is still somewhat computationally complex and time intensive, leaving room for the development of simpler time-saving techniques.

The present invention contemplates a new and improved image reconstruction technique which overcomes the above-referenced problems and others.

SUMMARY OF THE INVENTION

In accordance with one aspect of the present invention, a method of image reconstruction from wedge beam data is provided. The method includes collecting cone beam data in two-dimensional arrays. The collected data corresponds to rays of penetrating radiation diverging in two dimensions from a common vertex as the vertex travels along a curve. Each element of the data is related to line integrals of an object being reconstructed taken along each ray. A local coordinate system is defined having three mutually orthogonal axes and an origin at the vertex. The third axis of the local coordinate system extends in a direction tangential to the curve at the vertex. The collected data is rebinned into a wedge beam format wherein sets of parallel rays are grouped to define planes of radiation that angularly diverge from a common axis. A one-dimensional convolution of the rebinned data is computed in the local coordinate system along a direction parallel to the third axis. The convolved data is then weighted and three-dimensionally back-projected.

In accordance with a more limited aspect of the present invention, the common axis from which the defined planes angularly diverge is coincident with the third axis of the local coordinate system.

In accordance with a more limited aspect of the present invention, for each position of the vertex as it travels along the curve, the data collected is not truncated in a direction parallel to the tangent of the curve at the position of the vertex and is truncated in at least one other orthogonal direction.

In accordance with a more limited aspect of the present invention, the curve defines a helical path relative to the object.

In accordance with a more limited aspect of the present invention, the kernel for the one-dimensional convolution of the rebinned data is a ramp convolver.

In accordance with a more limited aspect of the present invention, the weighting of the convolved data is proportional to an average of values of a multiplicity function. The values correspond to planes containing a line extending from the vertex to a projection of a point of reconstruction on a plane defined by first and second axes of the local coordinate system.

In accordance with a more limited aspect of the present invention, values of the multiplicity function are determined based on a number of intersections their corresponding plane has with a portion of the helical path traveled by the vertex to collect enough data for reconstruction.

In accordance with a more limited aspect of the present invention, the values of the multiplicity function are equal to one divided by the number of intersections.

In accordance with a more limited aspect of the present invention, the portion of the helical path traveled by the vertex to collect enough data for rebinning into the wedge beam format extends from a point where the vertex is $-\pi/2$ revolutions away from an axial plane containing the point of reconstruction to a point where the vertex is $+\pi/2$ revolutions away from the axial plane containing the point of reconstruction.

In accordance with another aspect of the present invention, a CT scanner includes a first gantry which defines an examination region. A rotating gantry is mounted on the first gantry for rotation about the examination region. A source of penetrating radiation is arranged on the rotating gantry for rotation therewith. The source of penetrating radiation emits a cone-shaped beam of radiation that passes through the examination region as the rotating gantry rotates. A subject support holds a subject being examined at least partially within the examination region and at least one of the first gantry and the subject support is translated such that the subject passes through the examination region while the rotating gantry is rotated. In this manner, the source of penetrating radiation follows a helical path relative to the subject. A two-dimensional array of radiation detectors is arranged to receive the radiation emitted from the source of penetrating radiation after it has traversed the examination region. A reconstruction processor reconstructs images of the subject from data collected by the two-dimensional array of radiation detectors. The reconstruction processor includes a rebinning processor which rebins the data into a wedge beam format wherein sets of parallel rays of radiation are grouped to define planes of radiation that angularly diverge from a common axis which is tangential to the helical path. A convolver takes the data from the first data processor and performs a one-dimensional convolution on it in a local coordinate system along a direction which is tangential to the helical path. A data processor takes the data from the convolver and weights it. A backprojector then takes the data from the data processor and three-dimensionally back-projects it into an image memory. A human viewable display accesses the image memory to display reconstructed images of the subject.

One advantage of the present invention is increased efficiency in the reconstruction process.

Another advantage of the present invention is the simplification of the reconstruction.

Yet another advantage of the present invention is the achievement of high-quality images reconstructed from partial data sets, i.e., the data may be truncated in at least one direction without a loss of image quality.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
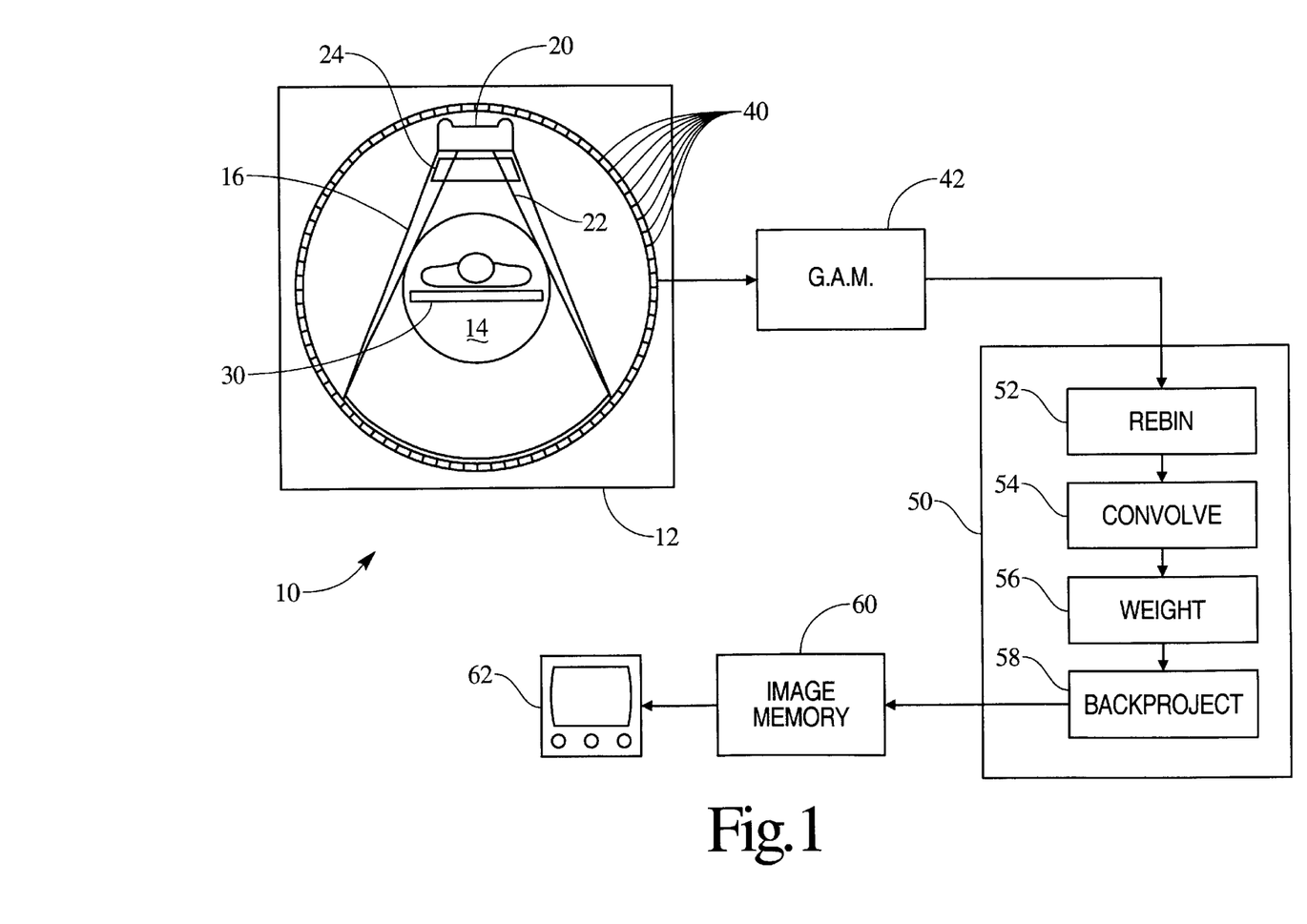
FIG. 1 is a diagrammatic illustration of a CT scanner in accordance with aspects of the present invention; and, FIGS. 2 through 4 are drawings used to illustrate the derivation and implementation of the reconstruction process in accordance with aspects of the present invention.

With reference to FIG. 1, a CT scanner 10 includes a stationary gantry 12 which defines an examination region 14. A rotating gantry 16 is mounted on the stationary gantry 12 for rotation about the examination region 14. A source of penetrating radiation 20, such as an x-ray tube, is arranged on the rotating gantry 16 for rotation therewith. The source of penetrating radiation produces a cone-shaped beam of radiation 22 that passes through the examination region 14 as the rotating gantry 16 rotates. A collimator and shutter assembly 24 forms the beam of radiation 22 and selectively gates the beam 22 on and off. Alternately, the radiation beam 22 is gated on and off electronically at the source 20.

A subject support 30, such as a couch or the like, suspends or otherwise holds a subject being examined or imaged at least partially within the examination region 14. Moreover, as the rotating gantry 16 rotates, the support 30, and consequently the subject thereon, are translated along a central horizontal axis of the examination region 14. In this manner, the source 20 follows a helical path relative to the subject. Optionally, in an alternative embodiment, the support 30 remains stationary while the "stationary gantry" 12 is translated or otherwise moved relative to the subject such that the source 20 follows a helical path relative thereto.

In the illustrated fourth generation CT scanner, a plurality of rings of radiation detectors 40 are mounted peripherally around the examination region 14 on the stationary gantry 12. Alternately, in a preferred embodiment, a third generation CT scanner is employed with the radiation detectors 40 mounted on the rotating gantry 16 on a side of the examination region 14 opposite the source 20 such that they span the area defined by the cone-shaped beam of radiation 22. Regardless of the configuration, the radiation detectors 40 are arranged such that a two-dimensional array thereof receive the radiation emitted from the source 20 after it has traversed the examination region 14.

In a source cone geometry, an array of detectors which span the radiation 22 emanating from the source 20 are sampled concurrently at short time intervals as the source 20 rotates behind the examination region 14 to generate a source view. In a detector geometry, the detectors are sampled a multiplicity of times as the source 20 rotates behind the examination region 14 to generate a detector view. The path between the source 20 and each of the radiation detectors 40 is denoted as a ray.

The radiation detectors 40 convert the detected radiation into electronic data. That is to say, each of the radiation detectors produces an output signal which is proportional to the intensity of received radiation. Optionally, a reference detector may detect radiation which has not traversed the examination region 14. A difference between the magnitude of radiation received by the reference detector and each active radiation detector 40 provides an indication of the amount of radiation attenuation along a corresponding ray of sampled radiation.

In source view geometry, each view or two-dimensional array of data represents a cone of rays having a vertex at the source 20 collected by a concurrent sampling of detectors.

A gantry acquisition memory board 42 receives sampled data from the radiation detectors 40. The gantry acquisition memory board 42 optionally performs an estimation of quantities proportional to line integrals of the scanned subject along rays joining the radiation source 20 to the detector and performs a ripple filtering operation before passing the data to an image processor 50. The image processor 50 processes the view data from the gantry acquisition board 42 and three-dimensionally backprojects it into an image memory 60.

The image processor 50 performs mathematical manipulations which convolve each view with an appropriate filter or convolution function for the view format. More specifically, a rebinning processor 52 rebins the data. In a preferred embodiment, no pre-weighting takes place before rebinning. A convolver 54 then performs a one-dimensional convolution. After a data processor 56 weights the convolved data, a backprojector 58 three-dimensionally backprojects the data into the image memory 60. A human viewable display 62, such as a monitor, accesses the image memory 60 to selectively display reconstructed images of the scanned subject.

Figure 2:
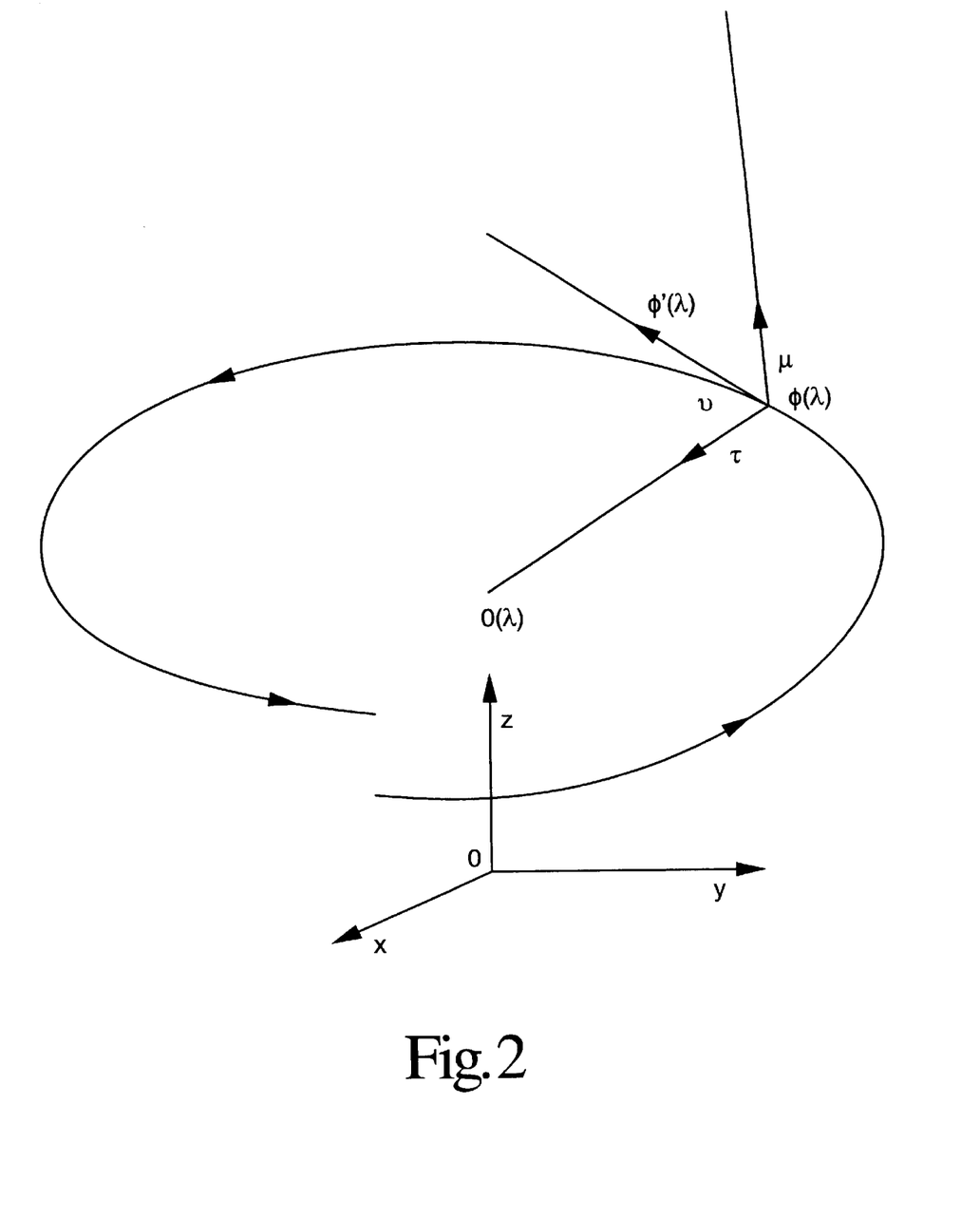
Figure 3:
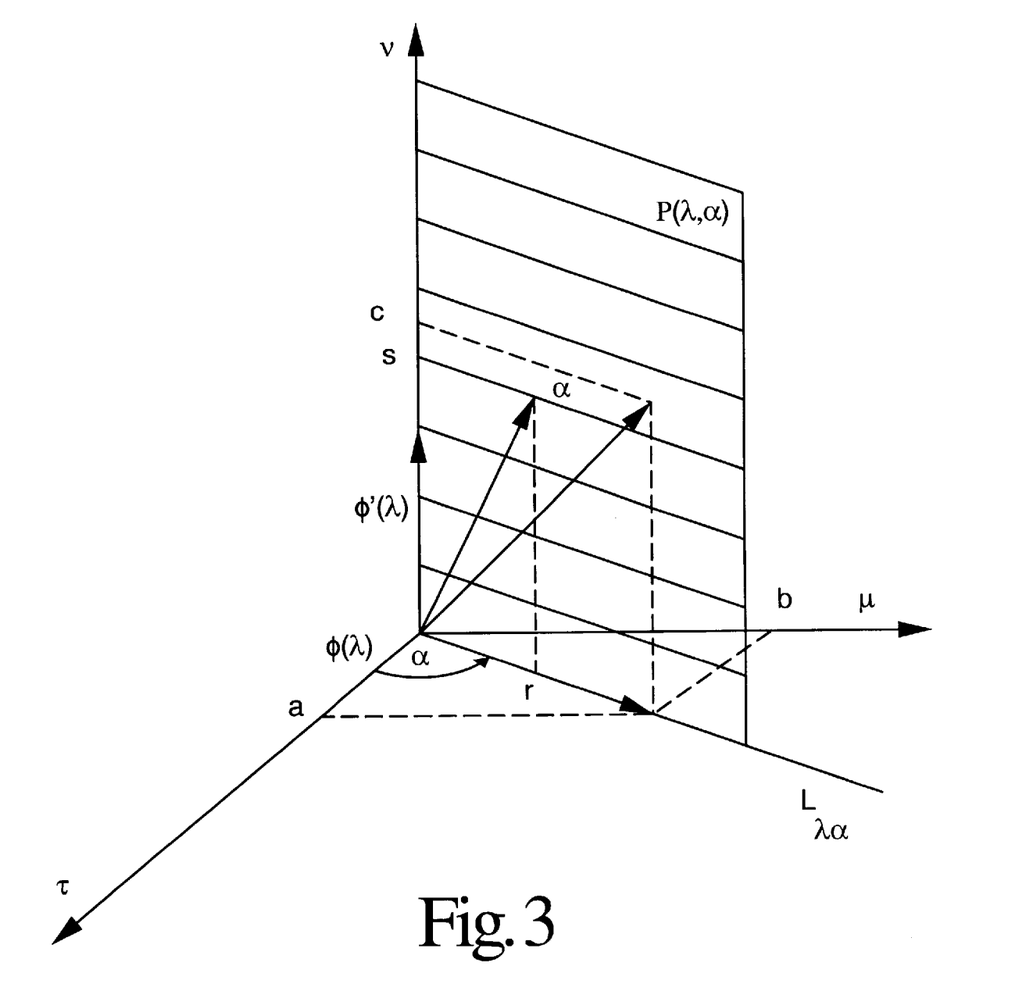
Figure 4:
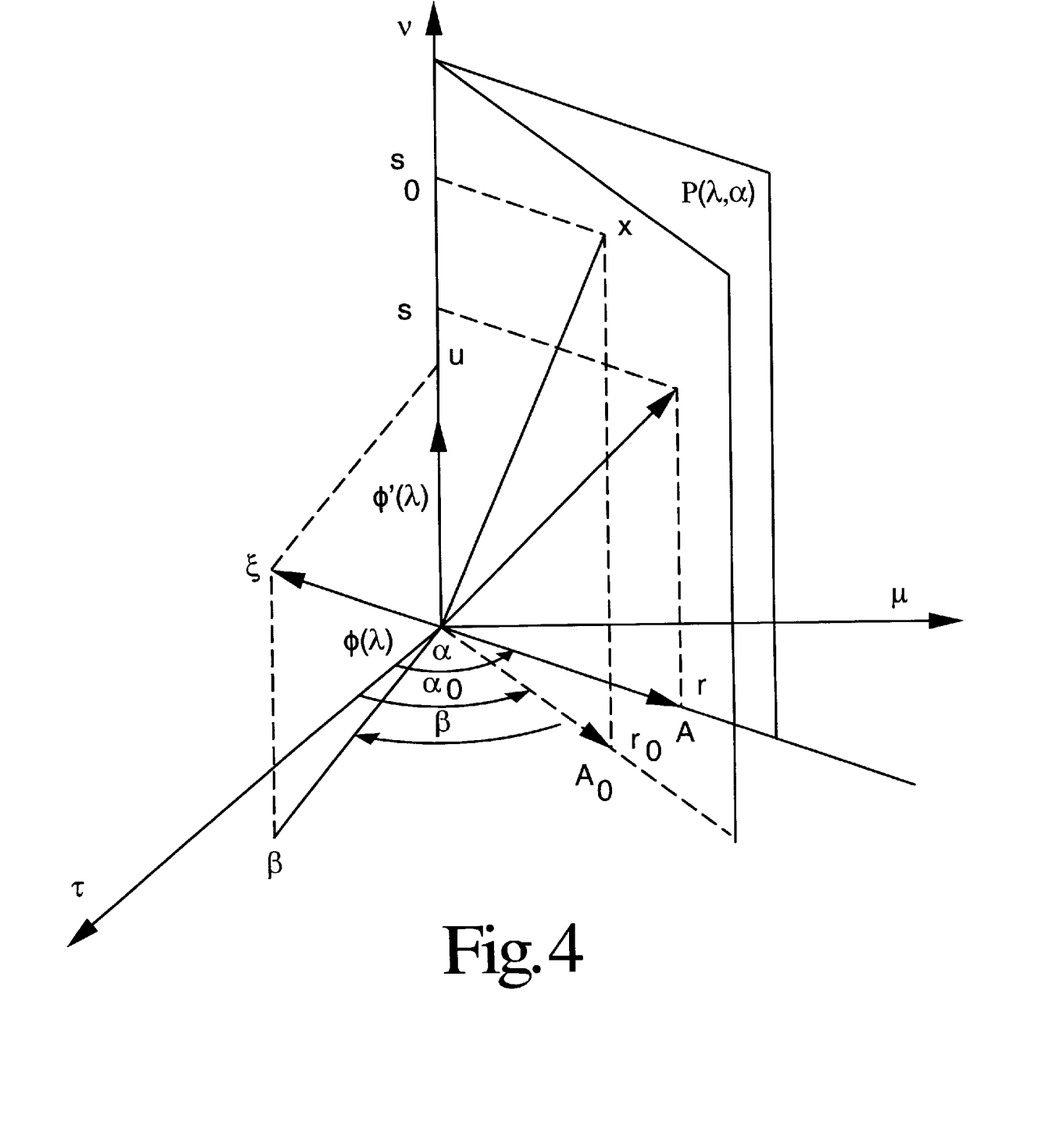

With reference to FIGS. 2–4 and continuing reference to FIG. 1, a detailed mathematical analysis of the reconstruction technique is presented. Keeping in mind the fact that the vertex of a partial cone beam (i.e., the source 20) describes a simple curve (i.e., a helix), the beam is rebinned so that the rays of the underlying geometry are parallel in one direction only, leaving the divergent nature of the beam in the orthogonal direction. This leads to a beam which is wedge shaped. A more rigorous definition of such a beam geometry is given below. Moreover, an exact reconstruction formula is obtained for this wedge beam geometry. Using a rigorous mathematical derivation, a very practical reconstruction procedure is derived. Ultimately, the reconstruction of the scanned object is done by performing a 3D backprojection of weighed 1D convolved data. More technical details are given below.

The terms and notation for the rigorous mathematical derivation of the aforementioned exact inversion formula are as follows: the subject to be reconstructed is represented by a function f from $R^3$ to $R$, and is of finite extent, i.e. of compact support; the unit sphere in $R^3$ is denoted by $S$, i.e. $S=\{x \in R^3 | \|x\|=1\}$; the inner product of two points x and y in $R^3$ will be denoted by $<x, y>$.

In the following, a cylindrical coordinate system is often used. A point x in $R^3$ with the following cylindrical coordinates (r, $\alpha$, s) is a point with Cartesian coordinates $x=r\cos\alpha$, $y=r\sin\alpha$, and $z=s$. For the sake of convenience, this point x in $R^3$ is at times denote by its polar angle $\alpha$.

The Fourier transform of a function h will be denoted by $\hat{h}$. For the 3D real function f, its Fourier transform is given by:

$$\hat{f}(\xi) = \int_{R^3} f(x) e^{-2i\pi \langle x,\xi \rangle} \, dx; \quad (1)$$

and expressing equation (1) in the cylindrical coordinate system, gives:

$$\hat{f}(\xi) = \int_{-\infty}^{\infty} \int_{-\infty}^{\infty} \int_{\pi}^{\pi} |r| f(r\cos(\alpha), r\sin(\alpha), s) e^{-2i\pi \langle \xi, \alpha \rangle} \, ds \, dr \, d\alpha. \quad (2)$$

The data is in the form of line integrals of the scanned subject f. Mathematically expressed, a positive half-line originating from a point V and extending in a direction $\alpha$, $\alpha \in S$, is the set $\{V+r\alpha | r \in [0,\infty)\}$ so that the integral of f along the half-line is expressed as:

$$p_V(\alpha) = \int_0^\infty f(V + r\alpha) \, dr. \quad (3)$$

From this point of view, the set $\{p_V(\alpha) | \alpha \in S\}$ represents the set of line integrals of f in a cone of vertex V. Due to the finite extent of the function f, there exits a cone defined by a subset C of S such that $p_V(\alpha)=0$ if $\alpha$ is outside of C, assuming that the vertex V is outside of the support of the function f.

In the following, a differentiable curve $\phi$ in $R^3$ is a differentiable function from an interval $\Lambda$ into $R^3$. A helix is an example of such a curve. For each point $\phi(\lambda)$ of the curve, a local orthonormal coordinate system is defined with the origin located at $\phi(\lambda)$, see FIG. 2. In the case of a helix defined by $\phi(\lambda)=(R\cos\lambda, R\sin\lambda, \sigma\lambda)$, an example of such a local coordinate system is the system defined by the following three unit orthonormal vectors:

$$\tau = (\cos\lambda, \sin\lambda, 0), \quad (4)$$

$$\mu = (-\sigma\sin\lambda, \sigma\cos\lambda, -R) / \sqrt{R^2 + \sigma^2}, \text{ and} \quad (5)$$

$$\nu = (-R\sin\lambda, R\cos\lambda, \sigma) / \sqrt{R^2 + \sigma^2}. \quad (6)$$

Note that the vector $\nu$ is a vector in the direction of the tangent to the helix at $\phi(\lambda)$. $T_\lambda$ denotes a rotation such that the transformation $\phi(\lambda)+T_\lambda$ brings the original Cartesian coordinate system into alignment with the local coordinate system. At each point $\phi(\lambda)$, a wedge beam transform of the function f is defined to be the function $g_\lambda$, defined in $R^3$ by the following equation:

$$g_\lambda(\alpha) = \int_{-\infty}^{\infty} f(\phi(\lambda) + T_\lambda(tr\cos(\alpha), tr\sin(\alpha), s)) \, dt, \quad (7)$$

where $\alpha$ is a point in $R^3$. For each angle $\alpha$, $L_{\lambda\alpha}$ denotes the line in the plane defined by the first two axis of the local coordinate system, going through $\phi(\lambda)$ and making an angle $\alpha$ with the first axis, see FIG. 3. If r=1, then $g_\lambda(\alpha)$ is the integral of the function f along the line going through a point on the third axis of the local coordinate system, at a distance s from $\phi(\lambda)$, and parallel to the line $L_{\lambda\alpha}$. Consequently, if the angle $\alpha$ is constant, and s varies from $-\infty$ to $\infty$, $g_\lambda(\alpha)$ are integrals of f along a set of lines which are parallel to the line $L_{\lambda\alpha}$. These lines are in the plane $P(\lambda,\alpha)$ containing the third axis of the local coordinate system, and making an angle $\alpha$ with the plane defined by the first and third axis, see FIG. 3. The rotation which is the inverse of $T_\lambda$ is denoted by $\delta_\lambda$.

For simplification of the notation, an operation is introduced which is called the cylindrical multiplication on $R^3$ by a scalar. In this operation, the first two components of a point in $R^3$ are multiplied by the scalar, and the third component is left unchanged. This operation is coordinate system dependant. The symbol $\diamond$ is used for this operation with respect to the original coordinate system, and the symbol $\diamond_\lambda$ is used for the coordinate system which is a rotation of the original coordinate system by $T_\lambda$. Equation (8) follows from the definition:

$$\rho \diamond_\lambda \alpha = \rho \diamond T_\lambda(\alpha). \quad (8)$$

Using this operation, the following are derived:

$$g_\lambda(\alpha) = \int_{-\infty}^{\infty} f(\phi(\lambda) + t \diamond T_\lambda(\alpha)) \, dt, \text{ or} \quad (9)$$

$$g_\lambda(\alpha) = \int_{-\infty}^{\infty} f(\phi(\lambda) + t \diamond_\lambda \alpha) \, dt. \quad (10)$$

In the following, $g_\lambda$ defined above is also denoted as $W_\lambda(f)$. From this point of view, $W_\lambda$ is considered as an operator or transformation acting on a set of functions in $R^3$. The family $\{W_\lambda\}$ of the operators $W_\lambda$, for $\lambda \in \Lambda$ is called the wedge beam transform. The family $\{W_\lambda f\}$ is referred to as the wedge beam data of f.

Partial cone beam data $\{p_{\phi(\lambda)}\}$ is rebinned in order to produce a set of wedge beam data $\{W_\lambda f\}$ using an interpolation process. Under the classical sufficient condition for cone beam geometry, it is possible to reconstruct the function f from the wedge beam data. The following lemma is used in the recovery of f from its wedge beam transform.

As 3D functions, the Fourier transform of f and that of its wedge beam transform satisfy the following equation:

$$\hat{g}_\lambda(\xi) = \int_{-\infty}^{\infty} \hat{f}(\rho \diamond_\lambda \xi) e^{2i\pi\langle \phi(\lambda), \rho \diamond_\lambda \xi \rangle} d\rho. \quad (11)$$

Consequently, $$\hat{g}_\lambda(\partial_\lambda \xi) = \int_{-\infty}^{\infty} \hat{f}(\rho \diamond \xi) e^{2i\pi\langle \phi(\lambda), \rho \diamond \xi \rangle} d\rho. \quad (12)$$

From the definition of the Fourier transform, the following is obtained:

$$\hat{g}_\lambda(\xi) = \int_{R^3} g_\lambda(\alpha) e^{-2i\pi\langle \alpha, \xi \rangle} d\alpha. \quad (13)$$

Hence, $$\hat{g}_\lambda(\xi) = \int_{R^3} \int_{-\infty}^{\infty} f(\phi(\lambda) + t \diamond_\lambda \alpha) e^{-2i\pi\langle \alpha, \xi \rangle} dt d\alpha. \quad (14)$$

Making a change of variables defined by $x = \phi(\lambda) + t \diamond_\lambda \alpha$, and $\rho = 1/t$, and realizing that the Jacobian of the transformation is 1, the following is derived:

$$\hat{g}_\lambda(\xi) = \int_{-\infty}^{\infty} \int_{R^3} f(x) e^{-2i\pi\langle \rho \diamond_\lambda (x-\phi(\lambda)), \xi \rangle} dx d\rho. \quad (15)$$

Or, $$\hat{g}_\lambda(\xi) = \int_{-\infty}^{\infty} \int_{R^3} f(x) e^{-2i\pi\langle x-\phi(\lambda), \rho \diamond_\lambda \xi \rangle} dx d\rho. \quad (16)$$

Hence the lemma is proved.

From the lemma, it is deduced:

$$\hat{g}_\lambda(r \diamond_\lambda \xi) = \frac{1}{|r|} \hat{g}_\lambda(\xi), \quad (17)$$

since, $$\rho \diamond_\lambda (r \diamond_\lambda \xi) = (\rho r) \diamond_\lambda \xi. \quad (18)$$

Furthermore, by writing $\langle \phi(\lambda), \rho \diamond \xi \rangle = r\rho$, the following is obtained:

$$\langle \phi'(\lambda), \rho \diamond \xi \rangle d\lambda = \rho dr, \quad (19)$$

and in view of the above lemma, $$\hat{g}_\lambda(\partial_\lambda \xi) = \int_{-\infty}^{\infty} \hat{f}(\rho \diamond \xi) e^{-2i\pi r\rho} d\rho. \quad (20)$$

Consequently, $$\hat{f}(\rho \diamond \xi) = \int_{-\infty}^{\infty} \hat{g}_\lambda(\partial_\lambda \xi) e^{-2i\pi r \rho} dr. \quad (21)$$

Hence, $$\hat{f}(\rho \diamond \xi) = \frac{1}{|\rho|} \int_\lambda |\langle \phi'(\lambda), \rho \diamond \xi \rangle| M_\lambda(\rho \diamond \xi) \hat{g}_\lambda(\partial_\lambda \xi) e^{-2i\pi\langle \phi(\lambda), \rho \diamond \xi \rangle} d\lambda, \quad (22)$$

where the multiplicity function $M_\lambda$ is introduced to account for redundancy in the collected data. In a preferred embodiment, the multiplicity function $M_\lambda$ is used to normalize the integration and satisfies:

$$\int_\lambda |\langle \phi'(\lambda), \xi \rangle| M_\lambda(\lambda) \delta(\langle \phi(s) - \phi(\lambda), \xi \rangle) d\lambda = 1. \quad (23)$$

The above result is then rewritten as:

$$\hat{f}(\rho \diamond \xi) = \int_\lambda |\langle \phi'(\lambda), \rho \diamond \xi \rangle| M_\lambda(\rho \diamond \xi) \hat{g}_\lambda(\rho \diamond \partial_\lambda(\xi)) e^{-2i\pi\langle \phi(\lambda), \rho \diamond \xi \rangle} d\lambda. \quad (24)$$

In particular, by taking $\rho = 1$, $$\hat{f}(\xi) = \int_\lambda |\langle \phi'(\lambda), \xi \rangle| M_\lambda(\xi) \hat{g}_\lambda(\partial_\lambda(\xi)) e^{-2i\pi\langle \phi(\lambda), \xi \rangle} d\lambda. \quad (25)$$

The function f is reconstructed from its wedge beam transform by back-projecting three-dimensionally the 3D convolved data. More precisely, for any point x in $R^3$, $$f(x) = \int_{\lambda_x} (T_\lambda(W_\lambda(f)) * q_\lambda * I_\lambda)(x - \phi(\lambda)) d\lambda, \quad (26)$$

where: $\phi(\Lambda_x)$ is a sub-curve of $\phi(\Lambda)$ such that any plane going through x cuts the sub-curve at least at one point; $q_\lambda$ is the 3D inverse Fourier transform of the function $\xi \to |\langle \xi, \phi'(\lambda) \rangle|$; and, $I_\lambda$ is the 3D inverse Fourier transform of a multiplicity function $M_\lambda$, which satisfies the following equation:

$$\int_{\Lambda_s} |\langle \phi'(\lambda), \xi \rangle| M_\lambda(\theta) \delta(\phi(s) - \langle \phi(\lambda), \xi \rangle) ds = 1. \quad (27)$$

Here, $T_\lambda g$ is defined by the following equation:

$$T_\lambda g(\alpha) = g(T_\lambda(\alpha)). \quad (28)$$

From the inversion of the Fourier transform, the following is obtained:

$$f(x) = \int_{R^3} \hat{f}(\xi) e^{-2i\pi\langle x, \xi \rangle} d\xi. \quad (29)$$

In view of equation (25), the following is obtained:

$$f(x) = \int_{R^3} \int_\lambda |\langle \phi'(\lambda), \xi \rangle| M_\lambda(\xi) \hat{g}_\lambda(\partial_\lambda \xi) e^{2i\pi\langle \phi(\lambda), \xi \rangle} e^{-2i\pi\langle x, \xi \rangle} d\lambda d\xi. \quad (30)$$

Or, $$f(x) = \int_\lambda \int_{R^3} |\langle \phi'(\lambda), \xi \rangle| M_\lambda(\xi) \hat{g}_\lambda(\partial_\lambda \xi) e^{2i\pi\langle x - \phi(\lambda), \xi \rangle} d\xi d\lambda. \quad (31)$$

Hence the formula is proved by realizing that the inner integral of the above expression is the inverse Fourier transform of the functions evaluated at $x - \phi(\lambda)$, and that the inverse Fourier transform of $\hat{g}_\lambda(\delta_\lambda(\xi))$ at $\alpha$ is $g_\lambda(T_\lambda(\alpha))$. Note further that the last expression to compute f uses only a subcurve of $\phi(\Lambda)$ such that $<x-\phi(\lambda), \xi> = 0$, for $\xi \in R^3$, i.e. a subcurve $\phi(\Lambda_x)$ satisfying the first condition of equation (26) stated above.

The above inversion formula is now rewritten as:

$$f(x) = \int_{\Lambda_x} Q_\lambda(x-\phi(\lambda)) d\lambda, \tag{32}$$

where $$Q_\lambda = T_\lambda(W_\lambda(f)) * q_\lambda * I_\lambda. \tag{33}$$

The integration with respect to $\lambda$ is referred to as the 3D backprojection, and $Q_\lambda$ the convolved data at view $\phi(\lambda)$. As compared to the inversion formula for the partial cone beam, while similar terminology is used to describe the inversion formula for the wedge beam transform, in actuality there are significant differences between them. Again, to take advantage of the fact that the first convolver $q_\lambda$ is the inverse 3D Fourier transform of $|<\phi'(\lambda), \xi>|$, it is advantageous to compute the convolution for the backprojection in the local coordinate system with one of the axis being parallel to $\phi'(\lambda)$. This is one reason behind the choice of the local coordinate system mentioned earlier.

In this local coordinate system (t,u,v), $$q_\lambda(t, u, v) = -C\delta(t)\delta(u)\frac{1}{v^2}, \tag{34}$$

where C is a constant, since the third axis is parallel to $\phi'(\lambda)$. Consequently, if A is a point in 3D space with coordinates (a,b,c) in the local coordinate system, then:

$$T_\lambda(W_\lambda(f)) * q_\lambda(A) = \tag{35}$$

$$-C \int_{-\infty}^{\infty}\int_{-\infty}^{\infty}\int_{-\infty}^{\infty} h_\lambda(a-t, b-u, c-v)\delta(t)\delta(u)\frac{1}{v^2} dt\, du\, dv,$$

where, $$h_\lambda(A) = T_\lambda(W\lambda(f))\ (\delta_\lambda(A)) = W_\lambda f(A). \tag{36}$$

Hence, $$T_\lambda(W_\lambda f) * q_\lambda(A) = -C\int_{-\infty}^{\infty} h_\lambda(a, b, c-v)\frac{1}{v^2} dv. \tag{37}$$

If $P(\lambda,\alpha)$ denotes the plane defined by the point (a,b,o), and the third axis, see FIG. 3, and $w_{\lambda\alpha}(v)$ denotes the integral of the function f along the line in the plane $P(\lambda,\alpha)$ and going through the point (0,0,c), so that $w_{\lambda\alpha}$ is a parallel beam in the plane $P(\lambda,\alpha)$, then the following is obtain:

$$T_\lambda g_\lambda * q_\lambda(A) = \frac{C}{\sqrt{a^2+b^2}} w_{\lambda a} * q(c). \tag{38}$$

This last convolution is the classical convolution of parallel beam with the classical 2D reconstruction kernel, i.e., a ramp function, restricted in the plane $P(\lambda,\alpha)$. The above expression is rewritten as follows:

$$W_\lambda(T_\lambda(f)) * q_\lambda(r\cos\alpha, r\sin\alpha, s) = \frac{C}{r} w_{\lambda a} * q(s). \tag{39}$$

Denoting the convolution $W_\lambda(T_\lambda(f))*q_\lambda$ by $k_\lambda$, the convolution data is then written in cylindrical coordinate as:

$$Q_\lambda(x-\phi(\lambda)) = \tag{40}$$

$$\int_{-\pi}^{\pi}\int_{-\infty}^{\infty}\int_{-\infty}^{\infty} |r| k_\lambda(r, \alpha, s) I_\lambda(x-\phi(\lambda)-(r,\alpha,s)) dr\, ds\, d\alpha.$$

The multiplicity kernel $I_\lambda$ is the inverse 3D Fourier transform of the multiplicity function $M_\lambda$. Hence, $$Q_\lambda(x-\phi(\lambda)) = \int_{-\pi}^{\pi}\int_{-\infty}^{\infty}\int_{-\infty}^{\infty} |r| k_\lambda(r, \alpha, s) \tag{41}$$

$$\int_{R^3} M_\lambda(\xi) e^{-2i\pi(x-\phi(\lambda)-(r,\alpha,s),\xi)} d\xi\, dr\, ds\, d\alpha.$$

Letting $(r_0, \alpha_0, s_0)$ be the cylindrical coordinates of $x-\phi(\lambda)$, see FIG. 4, then if $A=(r, \alpha, 0)$, and $A_0=(r_0, \alpha_0, 0)$, the following is obtained:

$$x-\phi(\lambda)-(r, s, \alpha) = A_0 - A + (s_0-s)v. \tag{42}$$

Based on the definition of $M_\lambda$, the coordinate system of $R^3$ for the computation of $M_{s0}$ is chosen by rotating the local coordinate system about the third axis so that the first axis aligns with $\phi(\lambda)A_0$, as shown in FIG. 4. Using this new coordinate system, writing:

$$\xi = t\beta + uv, \tag{43}$$

with $\beta = (t\cos\beta, t\sin\beta, 0)$, the following is obtained:

$$<x-\phi(\lambda)-(r,s,\alpha),\xi> = <A_0-A, \beta> + (s_0-s)u. \tag{44}$$

By the choice of the coordinate system, $M_\lambda$ depends solely on the angle $\beta$, and hence is expressed as a Fourier series as a function of the angle $\beta$. Approximating $M_\lambda$ by the first term of the series, denoted by $m_\lambda(\alpha_0)$, its inverse Fourier transform, $I_\lambda$, is given by the following equation:

$$I_\lambda(X-\phi(\lambda)-(r,\alpha,s)) = \tag{45}$$

$$m_\lambda(\alpha_0) \int_{-\infty}^{\infty}\int_{R^2} e^{-2i\pi(\langle A_0-A,\beta\rangle+(s_0-s)u)} d\beta\, du.$$

Hence, $$I_\lambda(X-\phi(\lambda)-(r,\alpha,s)) = m_\lambda(\alpha_0)\delta(s-s_0)\delta(A-A_0). \tag{46}$$

Consequently, equation (41) is reduced to:

$$Q(x-\phi(\lambda)) \approx m_\lambda(\alpha_0) r_0 k_\lambda(r_0,\alpha_0,s_0). \tag{47}$$

Or, in view of equation (39):

$$Q_\lambda(x-\phi(\lambda)) \approx m_\lambda(\alpha_0) w_{\lambda\alpha_0} * q(s_0). \tag{48}$$

From the discussions above, the following is obtained:

$$f(x) \simeq \int_{\lambda_x} m_\lambda(\alpha_0) w_{\lambda\alpha_0} * q(s_0) d\lambda. \tag{49}$$

In other words, the reconstruction of the function f is obtained by summing up the weighted convolved data along all the rays of the wedge beam going through the point of reconstruction x as $\phi(\lambda)$, the center of the beam, describes the sub-curve $\phi(\Lambda_x)$. For each position $\phi(\lambda)$, the plane $P(\lambda, \alpha_0)$ denotes the plane going through the points x and $\phi(\lambda)$ and which is parallel to the tangent $\phi'(\lambda)$. Within this plane, all the rays are parallel to each other, and perpendicular to φ'(λ). The convolution is the classical convolution of the parallel rays in this plane with the classical reconstruction kernel, i.e., a ramp function. The weight $m_\lambda(\alpha_0)$ is the average of the function $M_\lambda(\xi)$, for all unit vector $\xi$ orthogonal to the line $\phi(\lambda)A_0$.

In this manner, images are reconstructed from helical partial cone beam scanner data by rebinning the data into wedge beam data first. For each point $\phi(\lambda)$ of the helix, wedge beam data consist of line integrals of the scanned subject along a set of parallel rays. All the rays are perpendicular to the tangent $\phi'(\lambda)$ to the helix at $\phi(\lambda)$. A local coordinate system is defined, with the origin at $\phi(\lambda)$, and the third axis being parallel to $\phi'(\lambda)$. Rays of the wedge beam are grouped into sets of rays in various planes $P(\lambda,\alpha)$, making an angle a with the plane defined by the first and third axis of the local coordinate system. These planes intersect each other along the third axis. The data in a parallel beam within each plane $P(\lambda,\alpha)$ is convolved one-dimensionally with the classical 2D reconstruction kernel. For each reconstruction point x in 3D space, a subcurve $\phi(\Lambda_x)$ is chosen to get a complete data set for the reconstruction. The center $\phi(\lambda_0)$ of this subcurve is the intersection of the curve $\phi(\Lambda)$ with the horizontal plane going through the reconstruction point x. The extreme points of the sub-curve (sufficient to support rebinning into the wedge beam format) are chosen to be $\phi(\lambda_0-\pi/2)$, and $\phi(\lambda_0+\pi/2)$. The reconstruction of the scanned subject f at the point x is obtained by summing the weighted convolved data along all the rays going through the point x as λ describes $\Lambda_x$. For each λ in $\Lambda_x$, the convolved data is the classical 1D convolved data in the plane $P(\lambda, \alpha_0)$ which contains the point x. The weight of the convolved data depends on the pitch of the helix, and is proportional to the sum of the multiplicity function along all the planes going through the line $\phi(\lambda)A_0$ where $A_0$ is the orthogonal projection of the reconstruction point x onto the plane defined by the first and second axis of the local coordinate system. In this particular case, we may choose a weight $C(\lambda)$ to be 1 for all λ in Λ, and consequently, $M_\lambda(\xi)$ to be equal to the inverse of the total numbers of the intersection points of the sub-curve $\phi(\Lambda_x)$ with the plane going through $\phi(\lambda)$ and perpendicular to the vector $\xi$.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of image reconstruction from wedge beam data comprising:
    (a) collecting cone beam data in two-dimensional arrays, said collected data corresponding to rays of penetrating radiation diverging in two dimensions from a common vertex as the vertex travels along a curve with each element of the data related to line integrals of an object being reconstructed taken along each ray;
    (b) defining a local coordinate system having three mutually orthogonal axes and an origin at the vertex, wherein a third axis thereof extends in a direction tangential to the curve at the vertex;
    (c) rebinning the collected data into a wedge beam format, wherein sets of parallel rays are grouped to define planes of radiation that angularly diverge from a common axis;
    (d) computing a one-dimensional convolution of the rebinned data in the local coordinate system along a direction parallel to the third axis;
    (e) weighting the convolved data; and,
    (f) three-dimensionally backprojecting the weighted convolution.

2. The method according to claim 1, wherein the common axis from which the defined planes angularly diverge is coincident with the third axis of the local coordinate system.

3. The method according to claim 2, wherein for each position of the vertex as it travels along the curve, the data collected is partial cone beam data which is not truncated in a direction parallel to the tangent of the curve at the position of the vertex and is truncated in at least one other orthogonal direction.

4. The method according to claim 3, wherein the curve defines a helical path relative to the object.

5. The method according to claim 4, wherein a kernel for the one-dimensional convolution of the rebinned data is a ramp convolver.

6. The method according to claim 5, wherein the weighting of the convolved data is proportional to an average of values of a multiplicity function, said values corresponding to planes containing a line extending from the vertex to a projection of a point of reconstruction on a plane defined by first and second axes of the local coordinate system.

7. The method according to claim 6, wherein values of the multiplicity function are determined based on a number of intersections their corresponding plane has with a portion of the helical path traveled by the vertex to collect enough data for reconstruction.

8. The method according to claim 7, wherein the values of the multiplicity function are equal to the inverse of the number of intersections.

9. The method according to claim 7, wherein the portion of the helical path traveled by the vertex to collect enough data for rebinning into the wedge beam format extends from a point where the vertex is $-\pi/2$ revolutions away from an axial plane containing the point of reconstruction to a point where the vertex is $+\pi/2$ revolutions away from the axial plane containing the point of reconstruction.

10. The method according to claim 1, wherein full cone beam data is collected in step (a).

11. A CT scanner comprising:
    a first gantry which defines an examination region;
    a rotating gantry mounted on the first gantry for rotation about the examination region;
    a source of penetrating radiation arranged on the rotating gantry for rotation therewith, said source of penetrating radiation emitting a cone-shaped beam of radiation that passes through the examination region as the rotating gantry rotates;
    a subject support which holds a subject being examined at least partially within the examination region, wherein at least one of the first gantry and the subject support is translated such that the subject passes through the examination region while the rotating gantry is rotated and the source of penetrating radiation follows a helical path relative to the subject;
    a two-dimensional array of radiation detectors arranged to receive the radiation emitted from the source of penetrating radiation after it has traversed the examination region;
    a reconstruction processor which reconstructs images of the subject from data collected by the two-dimensional array of radiation detectors, said reconstruction processor including;
        a rebinning processor which rebins the data into a wedge beam format such that sets of parallel rays of radiation are grouped to define planes of radiation that angularly diverge from a common axis which is tangential to the helical path;

a convolver which takes the data from the rebinning processor and performs a one-dimensional convolution on it in a local coordinate system along a direction which is tangential to the helical path;

a data processor which takes the data from the convolver and weights it; and, a backprojector which takes the data from the data processor and three-dimensionally backprojects it into an image memory; and, a human viewable display which accesses the image memory to display reconstructed images of the subject.

12. The CT scanner according to claim 11, wherein for each position of the source of penetrating radiation along the helical path, the data collected is not truncated in a direction parallel to the tangent of the helical path at the position of the source of penetrating radiation and is truncated in at least one other orthogonal direction.

13. The CT scanner according to claim 12, wherein the convolver employs a ramp function as a kernel for the one-dimensional convolution.

14. The CT scanner according to claim 13, wherein the data processor multiplies the data by a weight that is proportional to an average of values of a multiplicity function, said values corresponding to planes containing a ray extending from the position of the source of penetrating radiation to a projection of a point of reconstruction on a plane which contains the source of penetrating radiation and is normal to the common axis.

15. The CT scanner according to claim 14, wherein each value of the multiplicity function is determined based on a number of intersections its corresponding plane has with an amount of the helical path followed by the source of penetrating radiation, said amount allowing enough data collection for reconstruction.

16. The CT scanner according to claim 15, wherein the values of the multiplicity function are equal to one divided by the number of intersections.

17. The CT scanner according to claim 15, wherein the amount of the helical path followed by the source of penetrating radiation which allows enough data collection for rebinning into the wedge beam format extends from a point where the source of penetrating radiation is $-\pi/2$ revolutions away from an axial plane containing the point of reconstruction to a point where the source of penetrating radiation is $+\pi/2$ revolutions away from the axial plane containing the point of reconstruction.

* * * * *